(12) United States Patent
Flexman et al.

(10) Patent No.: US 11,527,321 B2
(45) Date of Patent: Dec. 13, 2022

(54) AUGMENTED REALITY FOR PREDICTIVE WORKFLOW IN AN OPERATING ROOM

(71) Applicant: KONINKLIJKE PHILIPS N.V., Eindhoven (NL)

(72) Inventors: Molly Lara Flexman, Melrose, MA (US); Ayman Alalao, Cambridge, MA (US); Ashish Panse, Burlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 314 days.

(21) Appl. No.: 16/478,133

(22) PCT Filed: Jan. 15, 2018

(86) PCT No.: PCT/EP2018/050816
§ 371 (c)(1),
(2) Date: Jul. 16, 2019

(87) PCT Pub. No.: WO2018/134143
PCT Pub. Date: Jul. 26, 2018

(65) Prior Publication Data
US 2020/0126661 A1    Apr. 23, 2020

Related U.S. Application Data

(60) Provisional application No. 62/447,081, filed on Jan. 17, 2017.

(51) Int. Cl.
*G16H 30/40* (2018.01)
*G06T 19/00* (2011.01)
(Continued)

(52) U.S. Cl.
CPC .......... *G16H 40/63* (2018.01); *A61B 90/361* (2016.02); *A61B 90/39* (2016.02);
(Continued)

(58) Field of Classification Search
None
See application file for complete search history.

(56) References Cited

U.S. PATENT DOCUMENTS 9,317,580 B2 * 4/2016 Cohen-Solal .......... G16H 70/20
2008/0128626 A1 * 6/2008 Rousso ................ G01T 1/2985
250/362

(Continued)

OTHER PUBLICATIONS

Bleser et al: "Cognitive Learning, Monitoring and Assistance of Industrial Workflows Using Egocentric Sensor Networks"; PLOS ONE, DOI:10,371, Jun. 30, 2015, pp. 1-41.

(Continued)

*Primary Examiner* — David H Chu (57) ABSTRACT

An augmented reality system includes a head-mountable augmented reality platform (152) having a display to provide guidance to a user. A prediction module (115) is trained in a procedure and is configured to predict a next activity in the procedure based on a current condition. An image generation module (148) is responsive to the prediction module to provide a visual cue of a predicted next activity to the user through the head-mountable augmented reality platform.

25 Claims, 4 Drawing Sheets

(51) Int. Cl.
*G06V 20/20* (2022.01)
*G16H 40/63* (2018.01)
*A61B 90/00* (2016.01)
*G02B 27/01* (2006.01)
*G06V 40/20* (2022.01)

(52) U.S. Cl.
CPC ........ *G02B 27/0172* (2013.01); *G06T 19/006* (2013.01); *G06V 20/20* (2022.01); *G06V 40/20* (2022.01); *G16H 30/40* (2018.01); *A61B 2090/365* (2016.02); *A61B 2090/3995* (2016.02)

(56) References Cited

U.S. PATENT DOCUMENTS

| | | | | |
|---|---|---|---|---|
| 2012/0101360 | A1* | 4/2012 | Virmani | A61M 13/003 600/407 |
| 2013/0105699 | A1* | 5/2013 | Asma | A61B 6/488 250/363.03 |
| 2013/0297331 | A1* | 11/2013 | Zuehlsdorff | G16H 40/20 705/2 |
| 2013/0311200 | A1* | 11/2013 | Cohen-Solal | G06Q 10/06 705/2 |
| 2013/0343514 | A1* | 12/2013 | Heuscher | A61B 6/032 378/16 |
| 2014/0037049 | A1* | 2/2014 | Langan | A61B 6/541 378/20 |
| 2014/0177935 | A1* | 6/2014 | Nair | A61B 8/0883 382/132 |
| 2014/0310595 | A1 | 10/2014 | Acharya et al. | |
| 2014/0378816 | A1* | 12/2014 | Oh | G01R 33/56509 600/407 |
| 2015/0081315 | A1* | 3/2015 | Baker | G16H 30/20 705/2 |
| 2015/0146007 | A1* | 5/2015 | Dusik | G06K 9/6202 348/161 |
| 2016/0078183 | A1* | 3/2016 | Trygstad | G16H 50/20 706/11 |
| 2016/0307459 | A1* | 10/2016 | Chestnut | G06F 3/14 |
| 2017/0075421 | A1* | 3/2017 | Na | G06T 7/74 |
| 2017/0337713 | A1* | 11/2017 | Hoelzer | G06T 11/003 |
| 2017/0352282 | A1* | 12/2017 | Anderson | G09B 5/02 |
| 2018/0061255 | A1* | 3/2018 | Ekambaram | G06Q 10/083 |
| 2018/0173417 | A1* | 6/2018 | Foresti | G06F 3/013 |
| 2018/0322627 | A1* | 11/2018 | Gerard | A61B 8/00 |
| 2019/0128986 | A1* | 5/2019 | Helle | G01R 33/56316 |

OTHER PUBLICATIONS

Dergachyova et al: "Automatic Data-Driven Real-Time Segmentation and Recognition of Surgical Workflow"; Int J Cars (2016), vol. 11, pp. 1081-1089.

Katic et al: "A System for Context-Aware Intraoperative Augmented Reality in Dental Implant Surgery"; Int J Cars (2015), vol. 10, pp. 101-108.

Yaniv et al: "Applications of Augmented Reality in the Operating Room"; Fundamentals of Wearable Computers and Augmented Reality, Second Edition, Aug. 2015, CRC Press, pp. 485-518.

* cited by examiner

AUGMENTED REALITY FOR PREDICTIVE WORKFLOW IN AN OPERATING ROOM

CROSS-REFERENCE TO PRIOR APPLICATIONS

This application is the U.S. National Phase application under 35 U.S.C. § 371 of International Application No. PCT/EP2018/050816, filed on Jan. 15, 2018, which claims the benefit of U.S. Provisional Patent Application No. 62/447,081, filed on Jan. 17, 2017. These applications are hereby incorporated by reference herein.

BACKGROUND

Technical Field

This disclosure relates to augmented reality systems and methods, and more particularly to systems and methods for behavior prediction based on history and preferences to improve workflow in an operating room environment.

Description of the Related Art

A hybrid operating room (OR) and catheter laboratory (cathlab) support a broad range of imaging protocols. The number and type of these protocols can be complicated to optimally find a correct protocol for each step of a procedure. In addition, challenges arise when attempting to introduce new protocols, features, and tools without assistance during a procedure.

In one example, interventional x-ray suites provide a huge range of features and tools to optimize imaging, acquire various image formats, and perform complex protocols. User interaction is typically performed via modules such as an imaging module, geometry module, xper module, and review module as well as through typical on-screen interactions via keyboard, mouse, and monitors (such as, data and review monitors). Some of these modules (typically the geometry, imaging, and xper modules are also present at a side table within the control room).

Augmented reality generally refers to a situation when a live image stream is supplemented with additional computer-generated information. The live image stream can be provided using cameras, smart phones, tablets, etc. This image stream is augmented by a display to the user.

SUMMARY

In accordance with the present principles, an augmented reality system includes a head-mountable augmented reality platform having a display to provide guidance to a user. A prediction module is trained in a procedure and is configured to predict a next activity in the procedure based on a current condition. An image generation module is responsive to the prediction module to provide a visual cue of a predicted next activity to the user through the head-mountable augmented reality platform.

Another augmented reality system includes a head-mountable augmented reality platform having a display to provide guidance to a user. One or more models store procedure activities, and a prediction module is trained in at least one procedure and configured to predict a next activity in the at least one procedure based on a current condition compared to the one or more models to determine a best model that fits current activities to predict the next activity or to guide a user through a sequence of activities in the at least one procedure. An image generation module is responsive to the prediction module to provide a visual cue of a predicted next activity to the user through the display of the head-mountable augmented reality platform.

A method for predicting a next step in an augmented reality system includes gathering data representing a current condition in a procedure using head-mountable augmented reality platform; predicting a next activity in the procedure based on the data of the current condition and stored historic data for past activities; and generating visual cues on a display in the head-mountable augmented reality platform to indicate a predicted next activity to the user.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems, devices and methods are provided for augmented reality learning and customization. Embodiments described herein provide predictive capabilities for augmented reality guidance associated with medical procedures or other work environment activities, e.g., in a manufacturing environment or the like. In particularly useful embodiments, a head-mounted display is employed, which can include display glasses, display lenses, contact lenses, head-mounted display screens, virtual reality fixtures with tablets, smart phones, etc.

If an operator employs augmented reality, then tracking of the user's view, gestures, and interaction with the imaging systems can be performed. From this information, the operator's way of working can be determined and modeled. The model and the procedure steps can then be employed to predict next steps for the same user or other user's. Cues and triggers can be visually displayed on the head-mounted display device to direct workflow or encourage proper procedure sequencing to improve workflow and reduce procedure times. In some embodiments, an augmented reality prediction system can assist with the introduction of new workflows, tools, devices and features. The augmented reality can also be employed as feedback information and provide suggestions to the user through an augmented reality interface.

In one embodiment, the augmented reality can be employed to predict next steps during a clinical procedure in the hybrid operating room or catheter lab. In such environments, there are numerous input modules, numerous buttons, dials, screens, keyboards, mice, remote controls, etc. The augmented reality prediction system reduces complication be providing guidance in predicting next actions to perform in an efficient and fast way. Since there are multiple imaging protocols that vary the parameters of imaging devices (e.g., frame rate, radiation intensity, subtracting on/off, etc.), selecting an optimal imaging protocol can lead to improved image quality and reduced dose to the patient and the staff. The augmented reality prediction system can provide guidance as to the optimal imaging protocol and settings needed to provide improved image quality and reduced dose. In addition, the augmented reality prediction system can assist users in learning new technologies, protocols, or features that otherwise would be can be difficult to learn, which could lead to lower adoption. The system can indicate virtually which switches, sliders, knobs, controls, etc. to adjust and by how much. Instructional images, sounds, videos, verbal or textual instruction can be displayed and displayed in convenient locations, as needed or desired.

It should be understood that the present invention will be described in terms of medical instruments; however, the teachings of the present invention are much broader and are applicable to any augmented reality instruments and procedures, including, e.g., procedures related to nuclear reactors, manufacturing environments, or any other environment or application where augmented reality can be employed. In some embodiments, the present principles are employed in tracking or analyzing complex procedures for biological or mechanical systems. In particular, the present principles are applicable to procedures for medical treatment or diagnoses in all areas of the body, human or otherwise, such as the heart, circulatory system, lungs, gastro-intestinal tract, excretory organs, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Figure 1:
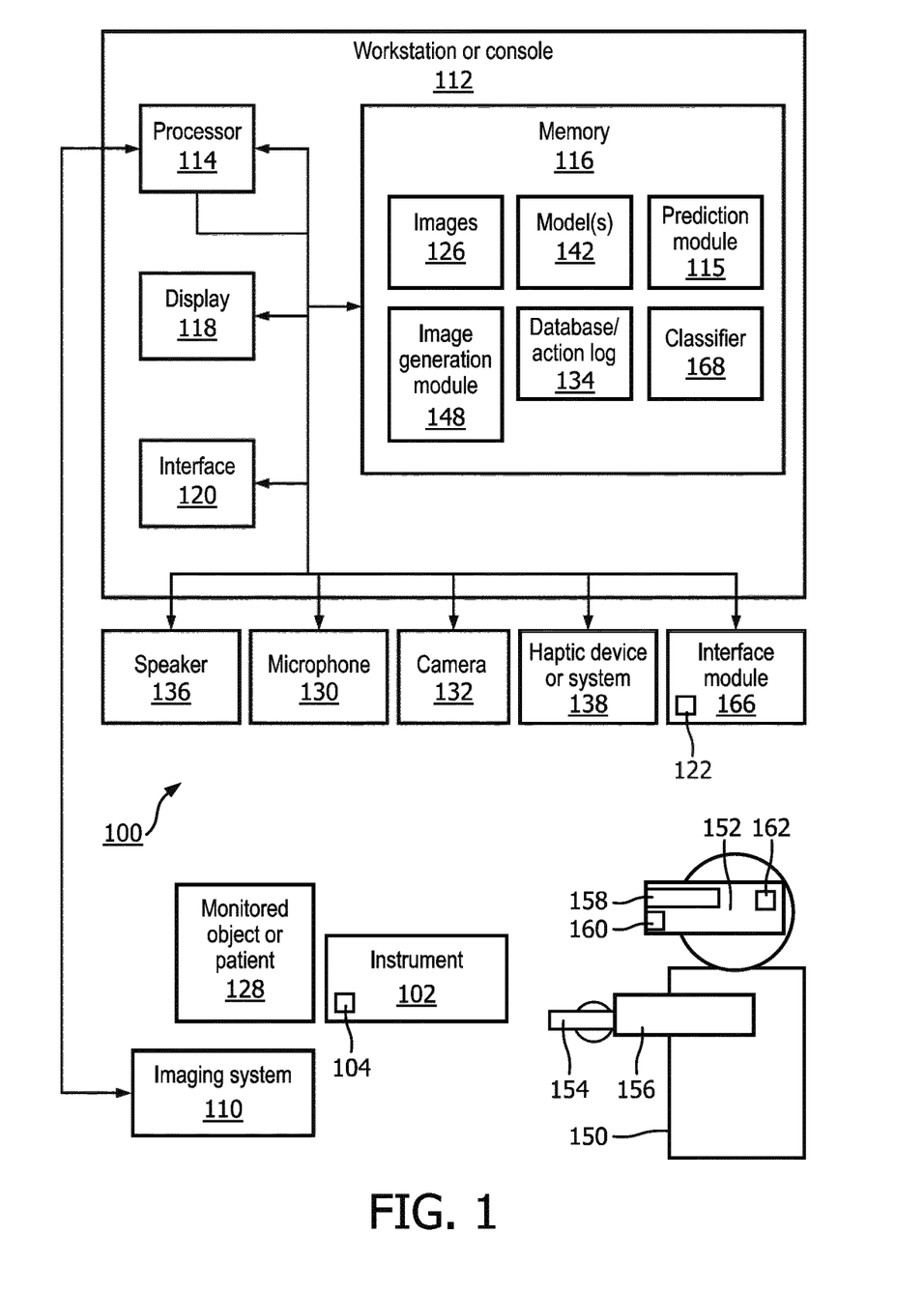
FIG. 1 is a block/flow diagram showing an augmented reality system with activity prediction or guidance in accordance with one embodiment.

Referring now to the drawings in which like numerals represent the same or similar elements and initially to FIG. 1, a system 100 for augmented reality prediction is illustratively shown in accordance with one illustrative embodiment. System 100 can include a collection of modules that can be integrated into a workstation 112, can include a single console or can include separate modules connected together. Workstation 112 preferably includes one or more processors 114 and memory 116 for storing programs and applications. Memory 116 may store a prediction module 115 configured to interpret feedback from one or more inputs to train a model or models 142 and to employ the model or models 142 for predicting (or guiding) future behavior based upon past events or event sequences.

The prediction module 115 employs historic data stored in a database or action log 134. This information may be employed to build one or more models 142. The action log 134 stores user activities during an augmented reality session. The action log 134 stores event data (e.g., temporal data, counts (number of times an action is performed (e.g., an event or procedure step)), the type of action, the source or equipment registering the action, the magnitude or characteristics of the action, the identity of the user, video or images of the action, etc. It should be understood that the types of inputs can vary widely depending on the applications, the equipment, the configuration of the environment, etc. The data entered into the action log 134 can be classified based on the input type or source; however, in a larger setting with a large number of inputs, a classifier or classification module 168 may be employed. The classifier 168 receives the inputs and tags the inputs for ease of use for model comparison and database storage. The prediction module 115 is configured to learn the proper performance of a procedure or procedures and may do in a plurality of ways. Each way may be configured or otherwise rely on a different set of inputs as needed or desired.

For example, in one embodiment, an augmented reality user 150 employs a head-mounted device 152. The device 152 can include any suitable head-mounted virtual reality system, e.g., GOOGLE GLASS™, HOLOLENS™, MAGIC LEAP™, VUSIX™, META™), and can include two or three-dimensional capability. The device 152 provides visual feedback in the form of overlays or other images or indicators to provide guidance to the user 150 during a procedure. The device 152 can also include a camera 158 or other sensor device or devices to provide feedback as to a current action or activity of the user 150. In one embodiment, virtual screens can be displayed in the device 152 (on the display) within the room in a smart or convenient location and at an appropriate time. These virtual screens can be generated as a predicted next setup or can be enabled manually or automatically in accordance with a user preference. The virtual screens can be moved in accordance with eye tracking to move the screens out of the way, or a virtual screen can be placed at a certain spot (e.g., on a wall or on a piece of equipment) at a designated time in the procedure.

In addition, data can be collected from a user who is using augmented reality that may include a plurality of sources, e.g., in a training mode. In one example, a camera feed of a user view and/or other view within the environment can be provided by camera 158 and by a remote camera(s) 132. Eye tracking and/or head tracking can be provided by retina tracking using the capabilities of the head-mounted device or using a retinal scanner 160 and/or one or more motion tracking devices 162, e.g., accelerometers, infrared tracking, optical fiber tracking, electromagnetic (EM) tracking or other tracking mechanism(s). In another embodiment, voice commands can be stored, modeled and employed for predicting actions or guiding future actions. A microphone 130 can be employed for recording the verbal commands, and a speaker 136 can be employed for providing feedback or guidance to the user to direct a next action in the sequence or provide warnings or advice for a next action or actions.

In another embodiment, hand gestures or body configurations can be employed to train and predict a next action. The hand gestures or body configuration can be determined using camera 132, by a remote tracking system (e.g. infrared camera), and/or a sensor or sensors 154 provided on the user 150. For example, a sensor 154 can be placed on an arm or hand 156 of the user 150 to track its motion. Any number of technologies as described here can be employed for gesture tracking.

The information received from one or more sources can be combined with other available data during the procedure. The database 134 and/or classifier 168 can organize the data into a procedural sequence of events. This sequence of events can be associated with a procedure (and other indicia, such as user ID, procedure variation types, etc.) and called up when a familiar action sequence is detected to guide a user in augmented reality through the rest of the procedure or to change settings as needed or desired during the procedure.

By way of example, a user can train the system 100 by conducting a medical procedure on a patient or other monitored object 128 (e.g., a physical training model). An imaging system 110 can include an x-ray system, ultrasound system, computed tomography (CT) system, magnetic resonance (MR) system, etc. In one embodiment, the imaging system 110 include a C-arm x-ray system. The procedure may call for a user 150 to focus their eye on a display 118 for an amount of the time when x-ray images 126 are being gathered, or the user 150 may change their focus a number of times between the display 118 and an interface module 166, which is employed for controlling x-ray image modes, x-ray exposure conditions, view settings, etc. The system 100 can sense the gaze of the user 150 on display 118, record the display imaging mode from the display 118 and employ other data such as hand motion, settings of the interface module 166, etc. to associate these activities with a given procedure. This data is classified and associated using the database 134 and/or the classifier 168. The associated data can be employed to build a model 142 that can be associated with this procedure. The model 142 can include settings used, imaging modes employed over time, imaging parameters (e.g., fluoro flavor, contrast, frame-per second, etc.), device tracking information (e.g., of surgical tools, robots, imaging equipment, etc.), user gesture tracking, dose information (to patient, user and staff), etc. Once this data is collected and processed, the model 142 may be trained.

The model 142 can then be employed by the prediction module 115 to predict a next step in a procedure or provide guidance as to future settings or actions based upon the history stored by the model 142. The model 142 can be a simple list of steps and settings that are conveyed to the appropriate equipment and peripherals at the appropriate time, or it can be an elaborate catalog of a history of conditions that existed in previous performances (including device settings, images, videos, instrument identification, etc.). In a particularly useful embodiment, the steps, settings, equipment used, etc. are conveyed to the user 150 through their augmented reality display device 152. This can include text messages, color changes, intensity changes, audio feedback, videos, etc. In one embodiment, room layout/equipment setup for setting up a next procedure can be predicted, including optimal places for people to stand (based on radiation dosage information), optimal places for equipment, etc. This layout/setup information can be based upon past layouts or based upon optimizations run by the prediction module 115 to provide an efficient workflow for a given procedure.

For example, in preparation for a procedure, the system 100 monitors the activities of the user 150 to determine the appropriate settings for different equipment, etc. in accordance with the model 142. After a few activities, the system 100 can predict a next step or a next procedure sequence of steps. During x-ray imaging, the user 150 may be focused on the display 118 for a certain amount of time and change their gaze a number of times between the display 118 and the interface model 166. The interface module 166 can include one or more of a geometry module, an imaging module, a review module and/or an xper module, which can be present in an x-ray control room. The prediction module 115 would predict that a same procedure was being deployed as identified by the model 142. The system 100 would prompt the user 150 to perform a next task upon the completion of a previous task. The prediction can come in the form of a text message on the display device 152 or arrows or other graphics showing a next knob to turn or switch to throw. Any number of visual, audio or haptic triggers or feedback mechanisms can be deployed.

In one example, imaging view modes can be switched depending on the steps within a procedure. For example, the mode or display 118 can be switched from e.g., a digital subtraction angiography (DSA) mode, which is a type of fluoroscopy technique used in interventional radiology to visualize blood vessels in a bony or dense soft tissue to a full 3D view for a transesophageal echocardiogram (TEE) ultrasound image mode. Selected imaging parameters can be switched or indicated in the augmented reality display 152 (e.g. frames-per-second, fluoro flavour for x-ray, depth, gain for ultrasound, etc.). User interactions with a specific software tool or hardware instrument 102 can be indicated or predicted (e.g., placing target markers in EchoNavigator™, VesselNavigator™) or predicting a next instrument to be used, etc. The next instrument can be located and highlighted in the augmented reality display 152 using, e.g., device tracking information (with e.g., Fiber-Optical RealShape™ (also known as "Optical Shape Sensing", "Fiber Shape Sensing", "Fiber Optical 3D Shape Sensing", "Fiber Optic Shape Sensing and Localization" or the like), In-Situ tracking (ultrasound), optical tracking, EM tracking, etc.) from a device tracker 104. In other embodiments, robotic positioning information of tools or imaging equipment can be employed.

The prediction module 115 employs the combination of data collected to generate a score for a plurality of possibilities for a next step. The highest score provides the most likely candidate model for a next step or actions. For example, one or more models 142 that store procedure activities can be determined by the prediction module 115 as to which model 142 best fits current activities. The best fit model can be employed to predict a next activity in the procedure. The prediction module 115 can include speech recognition, speech generation, speech-to-text generation, text generation and gesture recognition algorithms, as needed.

The predictive models 142, classifier module 168 and the prediction module 115 can employ one or more known learning techniques, such as, e.g., neural networks, multilayer perceptron (MLP), support vector machines (SVP), naïve Bayes, k-nearest neighbors, etc. The prediction module 115 can employ any suitable scoring method, e.g., maximum entropy, maximum likelihood, etc.

In one embodiment, workstation 112 includes an image generation module 148 configured to receive feedback from one or more sources and to provide text displays, graphic displays, intensity changes, etc. in the augmented reality display 152. The augmented reality display 152 can employ overlays or other rendering to provide guidance to the user 150 for the prediction of a next step.

The combination of information from one or more sources can be employed to learn and train models 142 during the procedure. The models 142 may learn the devices used at which points of the procedure, learn imaging modes/protocols employed during various phases of the procedure, understand a room layout during each phase of the procedure and its impact on workflow, learn where the user has difficulty with the workflow during the procedure, learn peak dose profiles at different locations in the room, etc. Once the system 100 has learned from the information, and a respective model or models 142 are created, the system 100 can start to predict and assist a user with the workflow.

The system 100 can suggest which imaging protocol to use next (or can have the next imaging protocol already pulled up as an option on the interface module 166 (which can include one or more display monitors). The system 100 can suggest optimizations to improve the image quality (e.g., gain, focus, depth, frame rate, etc.). The system 100 can keep an inventory of devices used during the procedure for inventory and billing purposes. The system 100 can suggest a next device to use, etc.

In particularly useful embodiments, the system 100 can suggest when there is an opportunity to reduce dose to the patient and/or staff by selecting a different protocol, fluoro flavor, c-arm position, or a different location for people standing in the room. The system 100 can bring up protocols, imaging data, device information, camera feeds, etc. at appropriate times based on past cases that were similar. Next steps can be predicted during a 'prescribed' workflow especially when the user is learning a new protocol, tool, or feature. In this case, the system 100 may not have learned the workflow but will have had it programmed to introduce the user to the new protocol, tool, or feature. The system 100 can bring up relevant screens like patient stats, dose information, different modality images, etc. based on historic data for that point in the procedure. The system 100 can also bring up references from similar cases based on what it has learned.

The system 100 can also be used to share feedback or prediction information with the user by a plurality of different modes or combinations of these modes. In one embodiment, an overlay image can be used in the display device 152 to guide the user to a next step, warn the user of something (proper procedure, what was done last time, etc.), display an image from a similar case, patient or scenario next to or on top of the live image for comparison; provide audio feedback to the user, provide haptic feedback using a haptic device or system 138 to the user.

The model or models 142 can be trained for a specific user, or can incorporate training information across multiple users, e.g., in a department, hospital, country, or globally. This can take into account variability in techniques across sites, privacy concerns, etc. In one embodiment, the learning from one operator or user may be used only to predict for that operator or user. In another embodiment, all learning for operators in a given hospital may be used to predict for an operator. In still other embodiments, all learning across the use of the system (globally) may be employed to predict for an operator. This could include cloud-based storage of the algorithm/data or network communication between locations.

The user can control the amount of prediction/suggestions by turning it up when they want more feedback or are trying a new task and want insights, or can turn it down if they are doing a highly unusual procedure where they do not want any suggestions. A prediction control 122 can be provided on the interface module 166, on an interface 120 or at any other convenient location to permit manual control of the prediction features. The control 122 can include variable levels of prediction suggestions or guidance based upon the desired levels of prediction or guidance of the user 150. The control 122 can be set to automatic, which triggers predictions and suggestions automatically based on the user's activities.

The user 150 can add additional training information as they become more familiar with the system 100. This may include adding additional voice commands/narrative during the procedure, making sure to capture device packaging in the camera view for device tracking, providing hand or other gestures to point at interesting or important things or to provide additional data to trigger the prediction module 115 to predict a next step. In this way, the user 150 can designate particular gestures or speech to identify particular steps in the procedure. This assists in training and more accurately predicting a next step.

At the end of the case or procedure, all of the information that was collected, particular models created, etc. can be saved as a 'case file'. This can be pulled up as a reference for future cases or can be used for training purposes. A user interface 120 can also allow the user to modify and improve the case file by adding additional notations, steps, and actions.

The present embodiments apply to the use of augmented reality in a cathlab or hybrid operating room to learn and predict workflow. The present embodiments are also applicable to, for example, mobile x-ray, ultrasound, MR, endoscopy, CT, etc. or any other procedure, commercial or industrial use, medical or otherwise.

Workstation 112 includes the display 118 for viewing images of a patient 128 or other subject. Display 118 may also permit a user to interact with the workstation 112 and its components and functions, or any other element within the system 100. This is further facilitated by the interface 120 which may include a keyboard, mouse, a joystick, a haptic device, or any other peripheral or control to permit user feedback from and interaction with the workstation 112.

Figure 2:
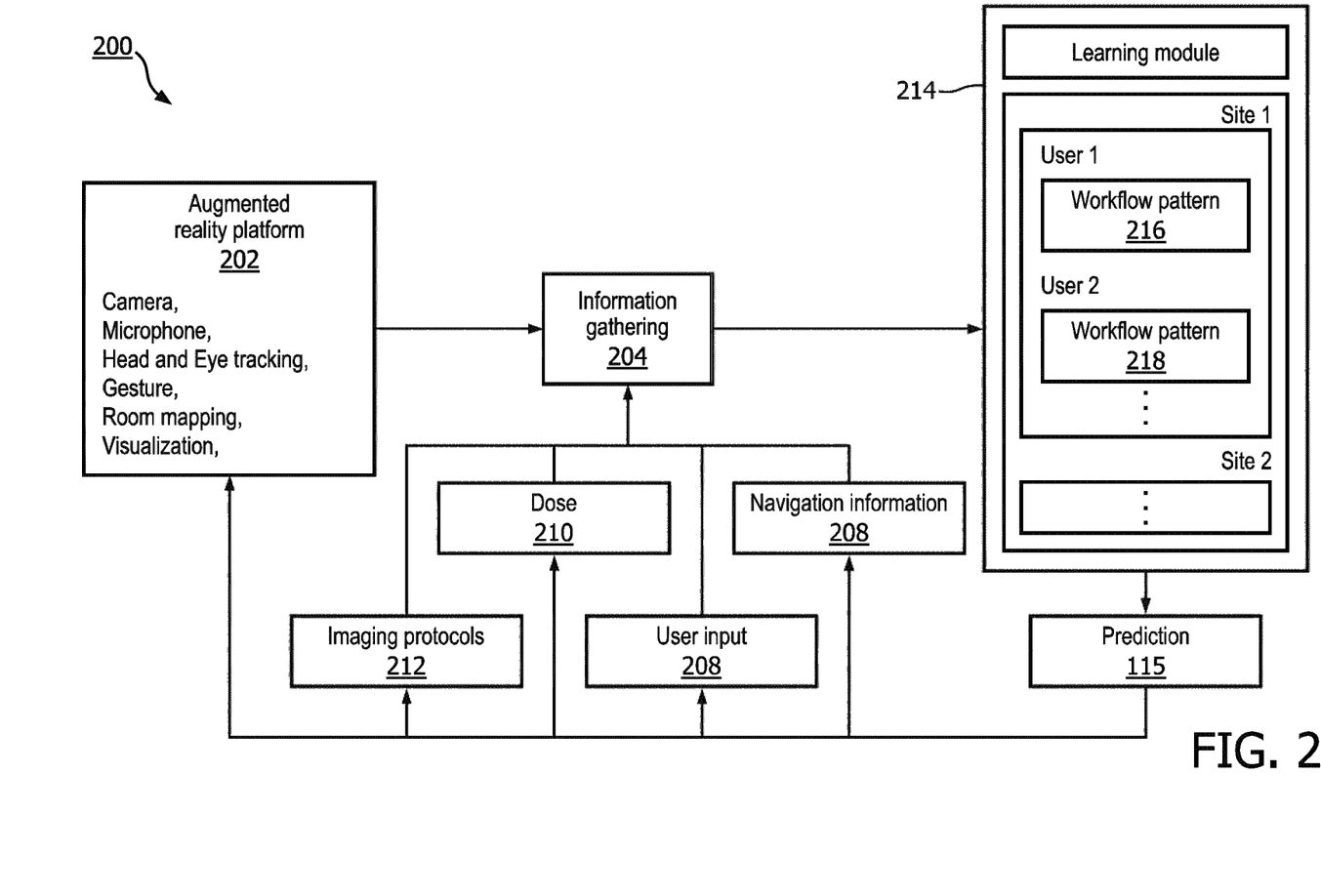
FIG. 2 is another block/flow diagram showing another augmented reality system including illustrative training inputs or current condition inputs in accordance with another embodiment.

Referring to FIG. 2, a block/flow diagram shows an augmented reality prediction system 200 in accordance with another embodiment. The system 200 includes an augmented reality platform 202. The platform 202 can include any number of components needed to provide an augmented reality interface. These components can include cameras, microphones, head and eye tracking devices, gesture recognition, room mapping applications, visualization devices (e.g., GOOGLE GLASS™, HOLOLENS™, MAGIC LEAP™, VUSIX™, META™ head-mounted smart phone or tablet displays, custom head-mounted displays. etc.). Information is gathered from the platform 202 and from other sources to learn activities and preferences associated with a procedure or other scripted activity.

The other sources can include information about imaging protocols 212, dose information 210, user input 208, navigation information 206, etc. The imaging protocols 212 can include imaging settings, views, type of imaging system (x-ray, etc.), etc. The dose information 210 can include radiation levels associated with equipment activities including imaging, subject setup and so forth. The dose information 210 can be useful in determining timing, but also useful as a metric for improving workflow (e.g., the lower doses being an improvement). User input 208 can include any user preference, limitation, warning or any other useful information. Navigation information 206 can include gestures, operating room navigation, instrument navigation or use, the head-mountable augmented reality platform movement, a patient position or movement, an imaging system position or movement and a position or movement of an instrument(s) employed in the procedure, etc. In addition, the navigation information 206 can include room layout information for setting up for a next procedure, including optimal places for people to stand (e.g., based on radiation dose), optimal places for equipment, etc. Other categories of information and parameters can also be employed instead of or in addition to those illustratively described.

Gathered information 204 (from one or more sources) is associated with or combined to create a profile or model of a particular activity in a learning module 214. In this embodiment, the learning module 214 can include some or all of the aspects of the classification module 168, the models 142 and the database 134, as described in FIG. 1. The learning module 214 executes one or more learning algorithms used to train models for predicting the next steps of a workflow with a given set of inputs from: the augmented reality platform 202, imaging protocols 212, dose information 210, user inputs 208, navigation information 206, etc. Computational saliency models can be employed to track where the user is looking. This along with gesture tracking can be employed to teach the learning module 214 to predict future moves.

In one example, predictive computer-vision can be employed as well to provide additional information about the activities associated with a procedural event or step. In one embodiment, visual representations of an image can be collected with a camera and employed to discover patterns and classify these patterns in bins or categories. This information will then be employed to classify future activities or employed in predicting next moves when similar behavior is encountered. Deep learning based goal recognition can also be used.

The learning module 214 creates associations between the different data sources to create models and/or associations. For example, for a given site (site 1, site 2), user 1 has a workflow pattern 216 including the information gathered during a procedure, and user 2 at site 1 has a different workflow pattern 218 for a same or different procedure. The patterns can be compared and combined (clusters) to form models (e.g., predictive models).

After sufficient training, the system can be exposed to a workflow. Based on comparisons different hypotheses can be determined for a predicted next step. These hypotheses can be scored against the model(s) to determine a most likely predicted next step by the prediction module 115. These predictions can be provided to any or all of the components to alter these components to ready them for a next step, or the prediction can simply be provided to the user wearing the augmented reality platform 202, who will act upon or be guided by the prediction.

Figure 3:
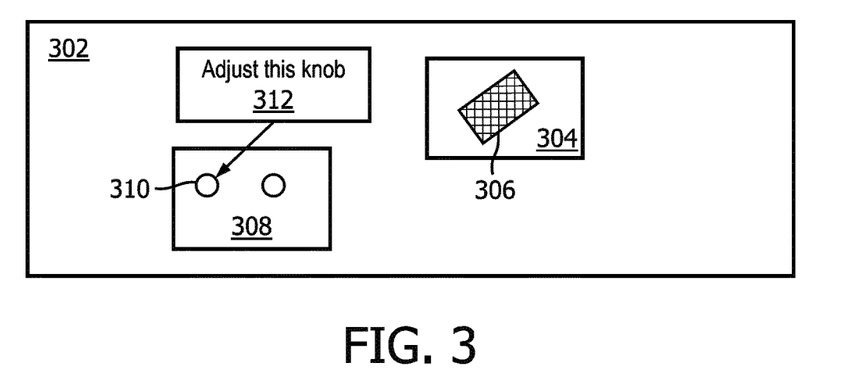
FIG. 3 is a diagram showing a view through a head-mounted display and indicating visual cues for a next activity in a sequence in accordance with one embodiment.
Figure 4:
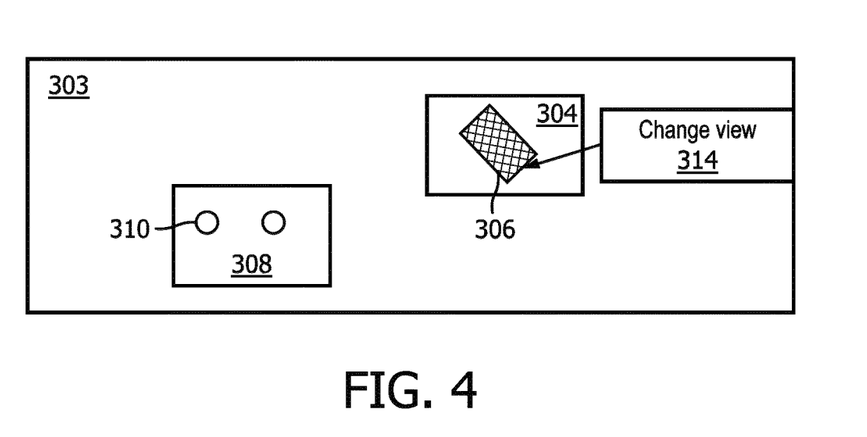
FIG. 4 is a diagram showing a subsequent view from FIG. 3 through the head-mounted display and indicating visual cues for a next activity in the sequence in accordance with one embodiment.

Referring to FIGS. 3 and 4, an illustrative view from a head-mounted display shows another aspect in accordance with the present principles. A view 302 from a head mounted display includes a real device 308 having a knob 310. Also shown is a real display 304 and an object 306 in the display 304 having a first orientation or imaging protocol. A text label 312 and an arrow are generated virtually to indicate to the user (e.g., wearer of the head-mounted display) that the predicted next step includes adjusting the knob 310.

In one embodiment, the display 304 or even the equipment 308 can be a virtual display or device generated automatically in accordance with a prediction or user preference. The next step or directions can be displayed in the views 302, 303 for performing a next action in the sequence. The virtual display 304 can display an image, video, graphic indicating useful information or providing guidance as needed or desired.

Once the knob 310 is adjusted, the system makes the next prediction. The next prediction here is to change to next view 303 in the display 308 as indicated in FIG. 4. This can be done automatically, or the system can provide a prompt, e.g., Change view 314, to change the view of the image 306 on the display 308. Any number of additional visual, voice, sound or haptic prompts can be employed.

Figure 5:
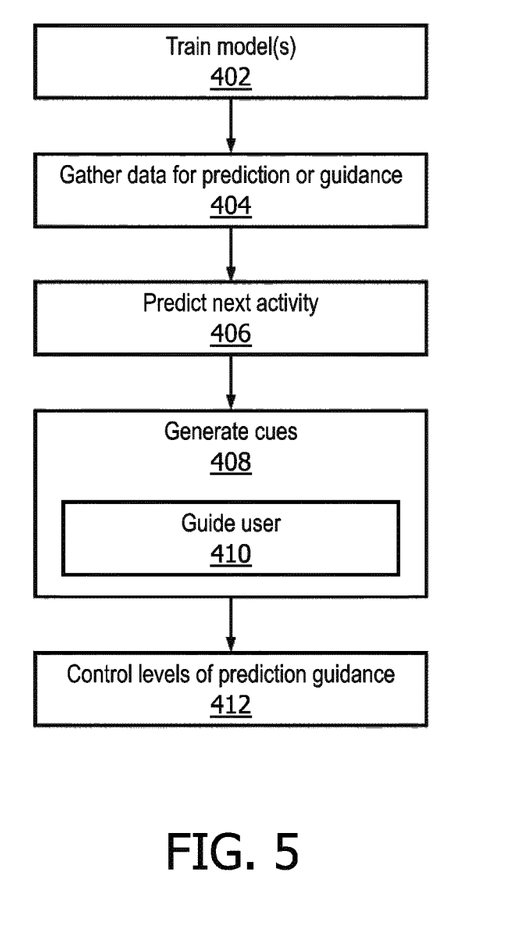
FIG. 5 is a flow diagram showing methods for activity prediction or guidance with an augmented reality system in accordance with illustrative embodiments.

Referring to FIG. 5, methods for prediction or guidance for a next step in an augmented reality system procedure are illustratively shown. In block 402, one or more models are trained by storing procedure activities (history) such that the one or more models can be employed to fit to a current activity sequence to predict the next activity in the procedure. The training step is optional for any particular procedure, and the models can be created and stored in a database at an earlier time.

In block 404, data representing a current condition in a procedure (and preferably corresponding to data stored in the models) is gathered using the head-mountable augmented reality platform and any other data gathering mechanism, e.g., microphone, cameras, dosimeter, navigational information, etc.

In block 406, a next activity is predicted or indicated (e.g., for guidance embodiments) in the procedure based on the data of the current condition and stored historic data for passed activities. The current condition can include at least one of a sequence of user actions, eye movement, head movement, gestures, eye focus, radiation dose information, and navigational information for at least one of the head-mountable augmented reality platform and an instrument employed in the procedure. User actions can include at least one of eye movement, head movement, gestures, equipment use and eye focus. Other information can be collected to evaluate the current condition and user actions as well, e.g., spatial information about the room or individuals, equipment types, etc.

In block 408, visual cues are generated on a display in the head-mountable augmented reality platform to indicate a predicted next activity to the user. In addition, non-visual cues or directions can also be generated by one or more feedback devices, e.g., speaker, haptic device, a display, etc. The visual cues can include automatically adding virtual screens to the room (through the head-mounted display) in smart places at the appropriate time, or moving a screen into a certain spot at a designated time in the procedure (e.g., to be out of the way, etc.).

In block 410, a user can be guided through a sequence of activities in the procedure using visual cues on the display in the head-mountable augmented reality platform. This can be in addition to or instead of the predicting of a next step. In one embodiment, activities can be stored from a user's perspective using a camera, and the user can be guided through a sequence of activities in the procedure with the head-mountable augmented reality platform using the activities stored by the camera. In this way, actual video can be employed to demonstrate the next step.

In block 412, the prediction or suggestion levels can be manually adjusted or set. This controls the prediction or guidance amount to assist in improving workflow especially for experienced users who may have performed a given procedure.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for augmented reality for predictive workflow in an operating room (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An augmented reality system for performing a clinical procedure on a patient using medical imaging according to a plurality of imaging protocols, the system comprising:
   a head-mountable augmented reality platform having a display viewable by a user;
   a memory configured to store one or more models comprising historic data of procedure activities; and
   a processor trained in procedures corresponding to the plurality of imaging protocols based on the historic data of procedure activities, the processor configured to:
   enable selection of an optimal imaging protocol from among the plurality of imaging protocols;
   during a procedure corresponding to the selected optimal imaging protocol:
   gather data representing a current condition associated with the selected optimal imaging protocol using the head-mountable augmented reality platform, and
   assess a plurality of possibilities for a next activity in the procedure or a next selected optical imaging protocol based on a correlation between the current condition and the one or more models;
   predict the next activity in the procedure corresponding to the selected optimal imaging protocol or the next selected optimal imaging protocol based on the assessment of the plurality of possibilities; and
   provide a visual cue on the display in the head-mountable augmented reality platform that guides the user to the predicted next activity.

2. The system as recited in claim 1, wherein the current condition includes a sequence of user actions to trigger a beginning of a session.

3. The system as recited in claim 2, wherein the user actions include at least one of eye movement, head movement, gestures, equipment use and eye focus.

4. The system as recited in claim 1, wherein the current condition includes dose information from an imaging modality.

5. The system as recited in claim 1, further comprising one or more feedback devices configured to provide non-visual cues or directions.

6. The system as recited in claim 1, wherein the processor is further configured to determine a model of the one or more models that fits current activities and apply the determined model to predict the next activity in the procedure corresponding to the selected optimal imaging protocol.

7. The system as recited in claim 1, wherein the processor is further configured to guide the user through a sequence of activities in the procedure corresponding to the selected optimal imaging protocol.

8. The system as recited in claim 1, further comprising a camera on the head-mountable augmented reality platform configured to provide visual information regarding activities from a user's perspective for guiding the user through a sequence of activities in the procedure corresponding to the selected optimal imaging protocol.

9. The system as recited in claim 1, wherein the current condition comprises at least one of a sequence of user actions, eye movement, head movement, gestures, eye focus, radiation does information, navigational information for at least one of the head-mountable augmented reality platform, and an instrument employed in the procedure.

10. The system as recited in claim 1, wherein a feature associated with the medical imaging that is improved by an adjustment to at least one setting of the selected optimal imaging protocol or different optimal imaging protocol is radiation dose of the medical imaging.

11. The system as recited in claim 1, wherein each imaging protocol includes at least one of a type of imaging system, an imaging setting, and a view.

12. A method for predicting a next step in an augmented reality system for performing a clinical procedure on a patient using medical imaging according to a plurality of imaging protocols, the method comprising:
   selecting an optimal imaging protocol from among the plurality of imaging protocols;
   gathering data representing a current condition in the selected optimal imaging protocol using a head-mountable augmented reality platform;
   during a procedure corresponding to the selected optimal imaging protocol:
      assessing a plurality of possibilities for a next activity in the procedure or a different selected optical imaging protocol based on a correlation between the current condition and one or more models;
      predicting the next activity in the procedure corresponding to the selected optimal imaging protocol or the different selected optimal imaging protocol based on the assessment; and
   generating visual cues on a display in the head-mountable augmented reality platform to guide a user to the predicted next activity.

13. The method as recited in claim 12, wherein the current condition includes at least one of a sequence of user actions, eye movement, head movement, gestures, eye focus, equipment use, radiation dose information, and navigational information for at least one of the head-mountable augmented reality platform, and an instrument employed in the procedure corresponding to the selected optimal imaging protocol.

14. The method as recited in claim 12, further comprising training the one or more models with the historic data for the past procedure activities, such that the one or more models are configured to fit a current activity sequence to predict the next activity in the procedure corresponding to the selected optimal imaging protocol.

15. The method as recited in claim 12, further comprising guiding a user through a sequence of activities in the procedure corresponding to the selected optimal imaging protocol using visual cues on the display in the head-mountable augmented reality platform.

16. The method as recited in claim 12, further comprising generating non-visual cues or directions by one or more feedback devices.

17. The method as recited in claim 12, further comprising:
   storing activities from a user's perspective obtained using a camera; and
   guiding the user through a sequence of activities in the procedure corresponding to the selected optimal imaging protocol with the head-mountable augmented reality platform using the stored activities.

18. The method as recited in claim 12, wherein a feature associated with the medical imaging that is improved by an adjustment to at least one setting of the selected optimal imaging protocol or different optimal imaging protocol is radiation dose of the medical imaging.

19. A non-transitory computer-readable storage medium having stored a computer program comprising instructions for performing a clinical procedure on a patient using medical imaging according to a plurality of imaging protocols, the instructions, when the computer program is executed by a processing circuitry, cause the processing circuitry to:
   select an optimal imaging protocol from among the plurality of imaging protocols;
   gather data representing a current condition in the selected optimal imaging protocol using a head-mountable augmented reality platform;
   during a procedure corresponding to the selected optimal imaging protocol:
      assess a plurality of possibilities for a next activity in the procedure or a different selected optical imaging protocol based on a correlation between the data representing the current condition and one or more models stored in memory,
      predict the next activity in the procedure corresponding to the selected optimal imaging protocol or in the different selected optimal imaging protocol based on the assessment; and
   generate visual cues on a display in the head-mountable augmented reality platform to guide a user to the predicted next activity.

20. The non-transitory computer-readable storage medium as recited in claim 19, wherein the current condition includes at least one of a sequence of user actions, eye movement, head movement, gestures, eye focus, equipment use, radiation dose information, and navigational information for at least one of the head-mountable augmented reality platform, and an instrument employed in the procedure corresponding to the selected optimal imaging protocol.

21. The non-transitory computer-readable storage medium as recited in claim 19, the instructions, when the computer program is executed by the processing circuitry, cause the processing circuitry to:
   train the one or more models with historic data of procedure activities, such that the one or more models are configured to fit a current activity sequence to predict the next activity in the procedure corresponding to the selected optimal imaging protocol.

22. The non-transitory computer-readable storage medium as recited in claim 19, the instructions, when the computer program is executed by the processing circuitry, cause the processing circuitry to:
- guide a user through a sequence of activities in the procedure corresponding to the selected optimal imaging protocol using visual cues on the display in the head-mountable augmented reality platform.

23. The non-transitory computer-readable storage medium as recited in claim 19, the instructions, when the computer program is executed by the processing circuitry, cause the processing circuitry to:
- generate non-visual cues or directions by one or more feedback devices.

24. The non-transitory computer-readable storage medium as recited in claim 19, the instructions, when the computer program is executed by the processing circuitry, cause the processing circuitry to:
- store activities from a user's perspective obtained using a camera; and
- guide the user through a sequence of activities in the procedure corresponding to the selected optimal imaging protocol with the head-mountable augmented reality platform using the stored activities.

25. The non-transitory computer-readable storage medium as recited in claim 19, wherein a feature associated with the medical imaging that is improved by an adjustment to at least one setting of the selected optimal imaging protocol or different optimal imaging protocol is radiation dose of the medical imaging.

\* \* \* \* \*